United States Patent [19]

Mai et al.

[11] Patent Number: 4,764,630
[45] Date of Patent: Aug. 16, 1988

[54] PREPARATION OF N,N-BIS-TRIALKYLSILYL CARBODIIMIDE

[75] Inventors: Khuong H. X. Mai, Waukegan; Ghanshyam Patil, Vernon Hills, both of Ill.

[73] Assignee: E. I. Du Pont de Nemours and Company, Wilmington, Del.

[21] Appl. No.: 127,764

[22] Filed: Dec. 2, 1987

[51] Int. Cl.$^4$ ................................. C07F 7/10
[52] U.S. Cl. ................................. 556/410; 556/404; 556/406
[58] Field of Search ................ 556/410, 404, 406

[56] References Cited

U.S. PATENT DOCUMENTS 3,352,799 11/1967 Klebe et al. ............... 556/410 X

Primary Examiner—Paul F. Shaver
Attorney, Agent, or Firm—Gildo E. Fato

[57] ABSTRACT

A process for the preparation of N,N'-bis-trialkylsilyl carbodiimide, according to the following schematic diagram:

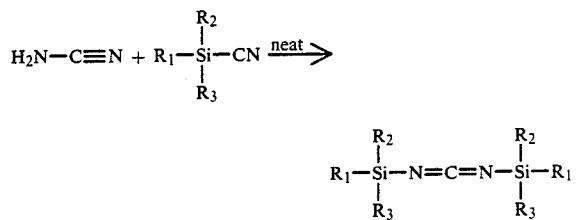

where $R_1$, $R_2$ and $R_3$ are each independently hydrogen, $C_1$–$C_{20}$ alkyl, $C_3$–$C_{12}$ cycloalkyl, $C_7$–$C_{15}$ aralkyl, unsubstituted or substituted aryl or heteroaryl or alternatively, $R_1$ and $R_2$ together with the silicon atom form a 3 to 12 member heterocyclic group, optionally including oxygen, sulfur, or phosphorus as a second heteroatom, the process comprising: reacting a trialkylsilyl cyanide with cyanamide as a neat mixture to prepare the desired N,N'-bis-trialkylsilyl carbodiimide. The reaction is practically complete in one minute. The compounds so prepared are intermediates in the preparation of polymers and precursors of carbodiimide.

4 Claims, No Drawings

PREPARATION OF N,N-BIS-TRIALKYLSILYL CARBODIIMIDE

BACKGROUND OF THE INVENTION

The present invention relates to a novel process for the preparation of N,N'-bis-trialkylsilyl carbodiimide. This compound is a very important starting material in the preparation of many polymers and also is a precursor of carbodiimide. There are a number of methods describing the preparation of N,N'-bis-trialkylsilyl carbodiimide, but as yet none provide a completely satisfactory procedure. In general, the literature methods required vigorous conditions such as the dehydration of bis-trialkylsilylurea using phenyl lithium (J. Pump, et al., Ann. 652, 21 1962), the reaction of hexamethyldisilazane with cyanogen chloride followed by rearrangement (J. Hundeck, CA. 65, 10606j), or the fusion of a mixture of trimethylsilyl chloride and calcium cyanamide (I. Vostokow, S.U. U.S. Pat. No. 906998 (1982)).

SUMMARY OF THE INVENTION

In accordance with one embodiment of the present invention, N,N'-bis-trialkylsilyl carbodiimides were prepared by reacting cyanamide with a trialkylsilyl cyanide with or without the presence of an aprotic solvent.

The process of the invention can be depicted by the following reaction scheme:

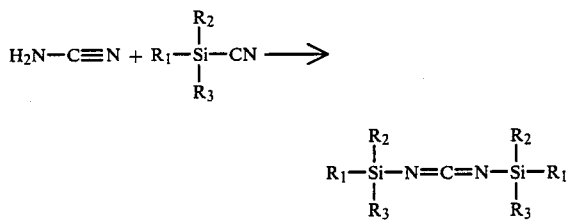

In the above scheme, $R_1$, $R_2$ and $R_3$ are each independently hydrogen, $C_1$–$C_{20}$ alkyl, $C_3$–$C_{12}$ cycloalkyl, $C_7$–$C_{15}$ aralkyl, unsubstituted or substituted aryl or heteroaryl or alternatively, $R_1$ and $R_2$ together with the silicon atom form a 3 to 12 member heterocyclic group, optionally including oxygen, sulfur, or phosphorus as a second heteroatom.

The term "alkyl" as used herein refers to straight or branched chain alkyl radicals containing from 1 to 20 carbon atoms including but not limited to methyl, ethyl, n-propyl, iso-propyl, n-butyl, sec-butyl, t-butyl, 2-methylhexyl, n-pentyl, 1-methylbutyl, 2,2-dimethylbutyl, 2-methylpentyl, 2,2-dimethylpropyl, n-hexyl, heptyl, octyl, nonyl, decyl, or elcosyl and the like.

The term "cycloalkyl" as used herein refers to cyclic saturated aliphatic radicals containing 3 to 12 carbon atoms in the ring, such as cyclopropyl, cyclobutyl, cyclopentyl, cyclohexyl, or cyclododecyl.

The term "aryl" represents phenyl or naphthyl which may be unsubstituted or substituted with loweralkyl of from 1 to about 6 carbon atoms, halo, hydroxy, amino, nitro, loweralkoxy, carboxy, loweralkanoyl, or loweralkoxycarbonyl.

"Heteroaryl" as used herein refers to radicals such as thiophene, furan, pyridine, or imidazole, which may be unsubstituted or substituted.

"Substituted aryl or heteroaryl" as used herein refers to aryl or heteroaryl substituted with loweralkyl, loweralkoxy, carboloweralkoxy, amido, or halo.

"Heteroatom" as used herein refers to atoms including oxygen, sulfur, nitrogen, or phosphorus.

In the process, cyanamide is mixed with trialkylsilyl cyanide as a neat mixture. A suitable temperature is 0° to about 150°, preferably at ambient temperature and a reaction time of 1 second to about 24 hours, preferably 1 to about 5 minutes.

In the described method, two equivalents of trialkylsilyl cyanide may be theoretically used for every one mole of cyanamide but it is preferable to use a slight excess amount of trialkylsilyl cyanide which functions both as reactants and solvent.

DETAILED DESCRIPTION OF THE INVENTION

In accordance with one embodiment of the present invention, the preparation of N,N'-bis-trialkylsilyl carbodiimide was conducted as follows:

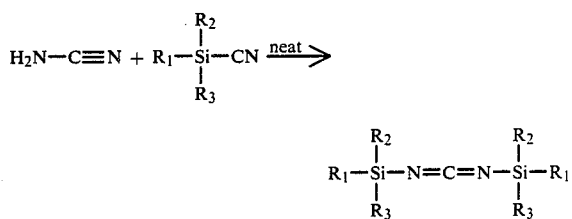

An example for the preparation of N,N'-bis-trialkylsilyl carbodiimide is as follows: Trimethylsilyl cyanide (24 g, 0.25 mole) was slowly added to cyanamide (4.4 g, 0.1 mole). An exothermic reaction with evolution of gaseous hydrogen cyanide was observed instantaneously. After the reaction subsided (1 minute), the mixture was distilled at atmospheric pressure to yield 22 g (92%) of the titled compound, b.p. 164° C. (750 mmHg), NMR (CDCl$_3$, TMS) 5 ppm 0.2 (sharp singlet), IR (neat), cm$^{-1}$ 2190. Analysis for $C_7H_{18}N_2Si_2$; Calculated: C %, 45.10; H %. 9.73; N %, 15.03; Foudn: C %, 44.99; H %, 9.62; N %, 14.88.

The process thus provides a very mild, convenient, simple and fast procedure for the preparation of N,N'-bis-trialkylsilyl carbodiimide.

What is claimed is:

1. A process for preparing a N,N'-bis-trialkylsilyl carbodiimide of the formula

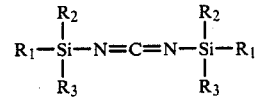

wherein $R_1$, $R_2$ and $R_3$ are each independently hydrogen, $C_1$–$C_{20}$ alkyl, $C_3$–$C_{12}$ cycloalkyl, $C_7$–$C_{15}$ aralkyl, unsubstituted or substituted aryl or heteroaryl or alternatively, $R_1$ and $R_2$ together with the silicon atom form a 3 to 12 member heterocyclic group, optionally including oxygen, sulfur, or phosphorus as a second heteroatom, which process comprises: mixing in a single reaction vessel a selected trialkylsilyl cyanide and cyanamide together to produce the desired N,N'-bis-trialkylsilyl carbodiimide.

2. The process of claim 1 wherein the reaction temperature ranges from about 0° to 150° for a time up to 24 hours.

3. The process of claim 2 wherein the reaction time ranges from about 1 to about 5 minutes.

4. The process of claim 3 wherein the reaction temperature is about ambient temperature.

* * * * *